(12) United States Patent
Zhu et al.

(10) Patent No.: US 9,993,202 B2
(45) Date of Patent: Jun. 12, 2018

(54) MULTI-LAYER PAD AND METHODS OF USING THE SAME

(75) Inventors: Boru Zhu, Granger, IN (US); Mihailo V. Rebec, Bristol, IN (US); Pamela J. Burson, Bristol, IN (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 2537 days.

(21) Appl. No.: 12/600,403

(22) PCT Filed: May 30, 2007

(86) PCT No.: PCT/US2006/062067
§ 371 (c)(1),
(2), (4) Date: Apr. 15, 2010

(87) PCT Pub. No.: WO2008/147347
PCT Pub. Date: Dec. 4, 2008

(65) Prior Publication Data
US 2010/0206746 A1    Aug. 19, 2010

(51) Int. Cl.
*A61B 5/00* (2006.01)
*A61B 5/145* (2006.01)
*A61B 5/1486* (2006.01)
*C12Q 1/00* (2006.01)
*G01N 33/52* (2006.01)

(52) U.S. Cl.
CPC .......... *A61B 5/6833* (2013.01); *A61B 5/1451* (2013.01); *A61B 5/1486* (2013.01); *A61B 5/14532* (2013.01); *A61B 5/14546* (2013.01); *C12Q 1/001* (2013.01); *C12Q 1/006* (2013.01);
(Continued)

(58) Field of Classification Search
USPC ................. 600/316, 345, 347, 365
See application file for complete search history.

(56) References Cited

U.S. PATENT DOCUMENTS 4,894,339 A * 1/1990 Hanazato et al. ............ 435/182
5,817,012 A   10/1998 Schoendorfer ............... 600/362
(Continued)

FOREIGN PATENT DOCUMENTS

| EP | 0304304 A2 | 2/1989 | ............. G01N 33/48 |
| EP | 1262559 A1 | 12/2002 | ............. G01N 33/52 |
| WO | WO 98/17995 | 4/1998 | |

OTHER PUBLICATIONS

Asakura et al., Immobilization of Glucose Oxidase on Nonwoven Fabrics with Bombyx mori Silk Fibroin Gel. Journal of Applied Polymer Science, vol. 46, 49-53 (1992).*

(Continued)

*Primary Examiner* — Etsub Berhanu
(74) *Attorney, Agent, or Firm* — Nixon Peabody LLP

(57) ABSTRACT

A multi-layer pad that is adapted to be used in determining an analyte concentration is disclosed. The multi-layer pad includes a first layer, a second layer, and a third layer. The first layer includes an enzyme wherein the enzyme is adapted to assist in determining the analyte concentration. The second layer is attached to a first surface of the first layer. The second layer is made of a skin-conforming material. The third layer is attached to a second surface of the first layer wherein the first layer is located between the second layer and the third layer. It is contemplated that the multi-layer pad may also be a two layer system.

20 Claims, 3 Drawing Sheets

(52) U.S. Cl.
CPC .... *G01N 33/525* (2013.01); *A61B 2562/0295* (2013.01)

(56) References Cited

U.S. PATENT DOCUMENTS

| | | | |
|---|---|---|---|
| 6,485,703 B1* | 11/2002 | Cote et al. | 424/9.1 |
| 7,045,054 B1 | 5/2006 | Buck et al. | |
| 2002/0099308 A1 | 7/2002 | Bojan et al. | 600/573 |
| 2003/0100846 A1 | 5/2003 | Custer et al. | |
| 2006/0195029 A1 | 8/2006 | Shults et al. | |
| 2006/0289307 A1* | 12/2006 | Yu et al. | 204/403.01 |
| 2007/0227907 A1* | 10/2007 | Shah et al. | 205/777.5 |
| 2008/0026473 A1* | 1/2008 | Wang et al. | 436/63 |
| 2008/0214918 A1* | 9/2008 | Brister et al. | 600/347 |

OTHER PUBLICATIONS

Rauf et al., Glucose oxidase immobilization on a novel cellulose acetate-polymethylmethacrylate membrane. Journal of Biotechnology, 121 (2006) 351-360.*
PCT International Search Report for International Application No. PCT/US/2006/062067 dated May 30, 2007 (4 pages).
PCT International Written Opinion for International Application No. PCT/US/2006/062067 dated May 30, 2007 (5 pages).
Extended European Search Report for European Application No. EP 12 18 5599.3-2319 dated Nov. 16, 2012 (4 pages).

* cited by examiner

MULTI-LAYER PAD AND METHODS OF USING THE SAME

CROSS-REFERENCE TO RELATED APPLICATIONS

This application is a National Stage of International Application No. PCT/US2006/062067, filed May 30, 2007, which is hereby incorporated by reference herein in its entirety.

FIELD OF THE INVENTION

The present invention relates generally to a multi-layer pad and methods of using the same. One or more layers of the multi-layer pad are hydrogels that are used to facilitate the analysis of analytes that are found in the skin.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered.

One non-invasive method for obtaining a sample without using a lancet is to take a transdermal sample of an analyte found in interstitial fluid (ISF). In this method, a composition, such as a hydrogel, is placed on the skin and assists in facilitating diffusion of analytes from a user's skin to a sensing instrument or meter, and in some cases (e.g., glucose) their subsequent products after enzyme-catalyzed reactions. An enzyme in the hydrogel composition assists in determining the analyte concentration of the sample. This composition desirably possesses sufficient mechanical and thermal stability to provide a relatively static, reactive and aqueous contact between the dermal sampling site and sensing instrument. One problem encountered with existing hydrogel compositions is the tendency of the enzyme to leach therefrom. It would be desirable to find a hydrogel composition that addresses such a problem.

SUMMARY OF THE INVENTION

According to one embodiment, a multi-layer pad is adapted to be used in determining an analyte concentration. The multi-layer pad includes a first layer and a second layer. The first layer includes an enzyme wherein the enzyme is adapted to assist in determining the analyte concentration. The second layer is attached to the first layer and is made of a skin-conforming material.

According to another embodiment, a multi-layer pad is adapted to be used in determining an analyte concentration. The multi-layer pad includes a first layer, a second layer, and a third layer. The first layer includes an enzyme that is adapted to assist in determining the analyte concentration. The second layer is attached to a first surface of the first layer and is made of a skin-conforming material. The third layer is attached to a second surface of the first layer and the first layer is located between the second layer and the third layer.

Additionally, a method of continuously determining an analyte concentration is disclosed. A multi-layer pad is provided and comprises a first layer and a second layer, wherein the second layer is attached to the first layer. The first layer includes an enzyme that is adapted to assist in determining the analyte concentration. The second layer is made of a skin-conforming material. A sensor that is adapted to assist in determining the analyte concentration is also provided. The multi-layer pad is placed on the skin and is located between the sensor and the skin. The method further includes the act of determining the analyte concentration.

In another embodiment, a method of continuously determining an analyte concentration is disclosed. A multi-layer pad is provided and includes a first layer, a second layer, and a third layer. The second layer is made of a skin-conforming material. The first layer includes an enzyme that is adapted to assist in determining the analyte concentration. The first layer is located between the second layer and the third layer. A sensor that is adapted to assist in determining the analyte concentration is also provided. The multi-layer pad is placed on the skin and is located between the sensor and the skin. The method further comprises the act of determining the analyte concentration.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

The present invention is directed to a novel multi-layer pad that is adapted to assist in determining an analyte concentration. The multi-layer pad exhibits desirable properties necessary for a transdermal method of determining analytes in one method. In one embodiment, the multi-layer pad is adapted to be used to assist in determining an analyte concentration of interstitial fluid (ISF) with a sensor. More specifically, the multi-layer pad is adapted to serve as an interface generally between and coupling the skin and the sensor.

Analytes that may be measured with a multi-layer pad include glucose, lipid profiles (e.g., cholesterol, triglycerides, LDL and HDL), microalbumin, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

Figure 1A:
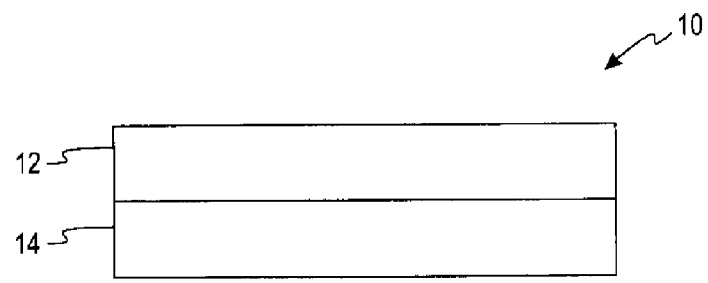
FIG. 1a is a two-layer pad according to one embodiment.

Referring initially to FIG. 1a, a multi-layer pad 10 is shown according to one embodiment. The pad 10 of FIG. 1a comprises a first layer 12 and a second layer 14. The first layer 12 is adjacent to the second layer 14.

The first layer 12 is generally a fabric, a porous membrane, or a paper material. The first layer 12 contains enzymes that may be added to the fabric, porous membrane, or paper material by several methods. For example, the enzymes may be physically absorbed and dried on or in the fabric, porous membrane, or paper material. Alternatively, the enzymes may be chemically immobilized to or within the fabric, porous membrane, or paper material.

The fabric may be made of several materials including, but not limited to, naturally occurring materials such as silk and cellulose, and synthetic polymeric materials such as polyethylene terephtalate, polyurethane, and glass fibers. To improve surface biocompatibility toward enzymes, the fabric materials may be pretreated with glow plasma, ion implantation, ozone, ultraviolet (UV), vacuum ultraviolet (VUV), chemical etching or surface modification, or pre-coated or grafted with hydrophilic polymers and/or proteins. It is contemplated that other materials may be used to form the fabric. One specific example of a polymer that may be used to form the fabric is polyethylene terephtalate fabric. However, it is contemplated that other polymeric materials may also be used to form the fabric.

The porous membrane may be made of several materials including, but not limited to, cellulose and its derivatives, nylon, polyacrylonitrile, polycarbonate, polypropylene, polysulfone, or polyvinyl chloride. To improve surface biocompatibility toward enzymes, the hydrophilic membranes may be pretreated with glow plasma, ion implantation, ozone, ultraviolet (UV), vacuum ultraviolet (VUV), chemical etching or surface modification, or pre-coated or grafted with hydrophilic polymers and/or proteins.

The paper material may be made of several materials including, but not limited to, cellulose and its derivatives. It is contemplated that other materials may be used to form the paper material. One specific example of such a paper material is Kimwiper® EX-L paper wiper from Kimberly-Clark. However, it is contemplated that other paper materials such as filter paper may be used.

The enzymes to be added to the fabric or paper material assist in determining the concentration of an analyte. Depending on the analyte, an enzyme may assist in converting the analyte into a species amenable to detection, such as electrochemical detection. One example of an enzyme that may be used in determining glucose is glucose oxidase. It is contemplated that other enzymes may be used to assist in determining glucose, such as glucose dehydrogenase. If other analytes are of interest, an appropriately selected enzyme may assist in determining the concentration of that analyte.

As discussed above, the enzyme can be physically adsorbed or chemically immobilized onto the fabric, membrane, or paper material that is to form the first layer 12. For physical adsorption, the enzyme may be dissolved into a buffer solution, for instance, phosphate-buffered saline solution. The first layer 12 may be formed by immersing the fabric, membrane or paper material in the enzyme-containing solution and subsequently dried. Water-soluble polymers may also be added into the enzyme solution prior to substrate immersion. Once the fabric, membrane or paper material is immersed into the enzyme solution, the water-soluble polymer may be adsorbed onto the substrate alone with the enzyme. Upon drying, the presence of the water-soluble polymer may enhance the physical entrapment of the enzyme.

For chemical immobilization, the enzyme may be fixed with a cross-linking agent such as glutaraldehyde. To improve enzyme activity, the enzyme may be pre-mixed with another protein such as albumin or gelatin. In another embodiment, a certain pre-treatment may be performed to introduce some functional groups, including amino or carboxyl, onto the surface of the substrate. The immobilization may also be done by forming chemical bonds between enzyme molecules and the substrate.

Besides enzymes, it is also contemplated that other materials may be included in the first layer 12 such as surfactants, polysaccharides, and salts, to enhance enzyme long-term stability.

The second layer 14 is made of a skin-conforming material. A "skin-conforming material" as defined herein includes materials that conform to the skin and maintain desirable contact with the skin. One non-limiting example of a skin-conforming material is a hydrogel. Other potential materials include porous polymers and spongy commercial materials, such as membranes that have a lot of open space that are soaked in a buffered liquid. Accordingly, in one embodiment, the second layer 14 is a hydrogel. The hydrogel should be able to maintain a water content from about 40% to about 98%, more desirably from about 80% to about 95%, to facilitate fast diffusion of analytes. The second layer 14 is a desirably optimized to have good biocompatibility for skin contact.

The second layer 14, in another embodiment, is a cross-linked hydrophilic polymer. In another embodiment, the second layer 14 may be a polymer with a certain hydrophilic and hydrophobic balance. To form a cross-linked polymer in one embodiment, the second layer 14 is polymerized from a monomer mixture or coated from a polymer solution. One specific non-limiting example of a monomer solution to form a cross-linked polymer includes N-vinyl pyrrolidone, vinyl acetate, diethylene glycol divinyl ether, and (2-hydroxy-4'-(2-hydroxyethoxy)-2-methylpropiopheone, which is an UV initiator, at a pre-determined ratio. It is contemplated that other cross-linked hydrophillic polymers may be formed using polyethylene glycol acrylates, acrylic acid, and acrylamide.

In the above described embodiment, an UV initiator may be used and therefore free-radical polymerization of the first layer 12 with the second layer 14 is initiated by UV irradiation. Other methods to initiate co-polymerization may also be used including thermal initiation (with thermal initiator), γ-ray, and electron beam (with or without initiator).

In another embodiment, the second layer 14 is formed from a coated polymer solution. One non-limiting example of a coated polymer solution includes the use of sodium alginate and poly(ethylene oxide). Alginate is a natural copolymer of two uronic acids, D-mannuronic acid and L-guluronic acid. One method to cross-link the polymer coating described above with the first layer 12 so as to form the second layer 14, is to associate the polymer solution with calcium ions. While not being bound by theory, calcium ions are believed to bind to the polymer when there are two neighboring guluronic acid residues. This binding forms an insoluble network.

It is contemplated that other materials may be used to form the second layer 14 such as ω-methoxy-α-(chloromethyl benzoyl) polyethylene glycol, a hydrophilic polymer with photo-sensitive functional groups. The cross-linking reaction may be initiated with UV irradiation to form the second layer 14 after a polymer solution is applied onto the first layer 12. In another embodiment, hydrophilic polymers in solution may be coated and dried on the first layer 12. The cross-linking reaction may be initiated with plasma exposure under inert gas such as, for example, argon or nitrogen. The cross-linking reaction may also be initiated with γ-ray, or an electron beam.

To provide and maintain openings formed in the skin, the second layer 14 may include a permeation enhancer. Non-limiting examples of permeation enhancers that may be used include squalene, unsaturated fatty acids, glycerol derivatives of fatty alcohols, dimethylsulfoxide, and alkyl esters of fatty acids. Furthermore, where desirable to keep the skin moist, the second layer 14 may also include humectants. Non-limiting examples of humectants that may be used in the second layer 14 include glycerol, hexylene glycol and sorbitol, maltitol, polydextrose, propylene glycol, lactic acid, and lactate metal salts. To assist the multi-layer pad 10 in obtaining desirable contact with the skin, the second layer 14 may also include surfactants. Non-limiting examples of surfactants that may be used include alkyl phenols such as TRITON® X-100 (octyl phenol ethoxylate having a molecular formula of $C_{14}H_{22}O(C_2H_4O)_n$ where an average "n" is 9 or 10), and sorbitol and sorbitol derivatives such as the TWEEN® series.

It is also contemplated that other materials may be included in the second layer 14. For example, an electrolyte may be included in the second layer 14. The electrolyte may perform multiple functions. First, the electrolyte is a chemical compound that ionizes when dissolved to produce an electrically-conductive medium. Second, the electrolyte desirably contains a high salt concentration so that when used in applications contacting the skin, it assists in exerting osmotic pressure on the skin. Thus, electrolytes are desired in skin-contacting layers such as the second layer 14. By exerting osmotic pressure on the skin, the electrolyte assists in driving out the interstitial fluid (ISF) that contains the analyte. Non-limiting examples of electrolytes that may be used include sodium and potassium salts of chloride, phosphate, citrate, acetate and lactate.

Figure 1B:
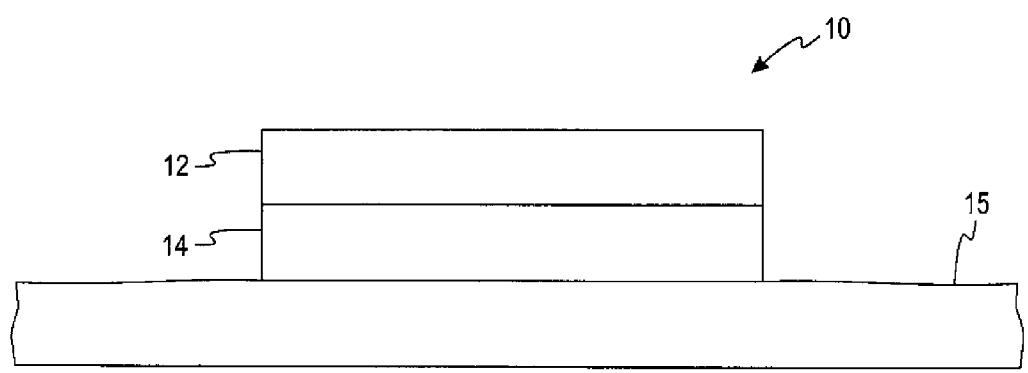
FIG. 1b is the two-layer pad of FIG. 1a applied to skin.

As discussed above, the multi-layer pad 10 of FIG. 1*a* may be applied to the skin. An example of the multi-layer pad 10 contacting skin 15 is shown in FIG. 1*b*.

Figure 2:
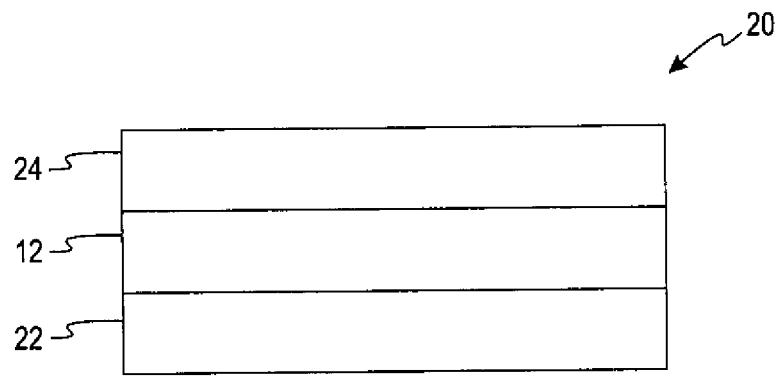
FIG. 2 is a three-layer pad according to one embodiment.

Referring now to FIG. 2, a multi-layer pad 20 is disclosed in another embodiment. The multi-layer pad 20 of FIG. 2 comprises a first layer 12, a second layer 22, and a third layer 24. The second layer 22 is adjacent to a first surface of the first layer 12 and the third layer 24 is adjacent to a second surface of the first layer 12. Thus, the first layer 12 with the enzyme is located between the second layer 22 and the third layer 24. By locating the enzymes in between the second layer 22 and the third layer 24, the ability to prevent or inhibit the enzymes from leaching is enhanced. Additionally, the skin interaction with the enzymes is also reduced or eliminated. If UV is used to initiate cross-linking reaction as described above in reference to FIG. 1*a*, the location of the enzymes in the first layer 12 may prevent or inhibit dramatic loss in activity thereto. Furthermore, by providing the first layer 12 between two opposing layers 22, 24, different materials may be selected to form the second layer 22 and the third layer 24. For instance, the second layer 22 may be optimized for skin contact while the third layer 24 may be optimized for the redox-reaction. The second layer 22 and the third layer 24 may be made of the materials that were described in reference to the second layer 14. The multi-layer pad 20 may also be applied to the skin in a similar manner as multi-layer pad 10 in FIG. 1*b*.

Figure 3:
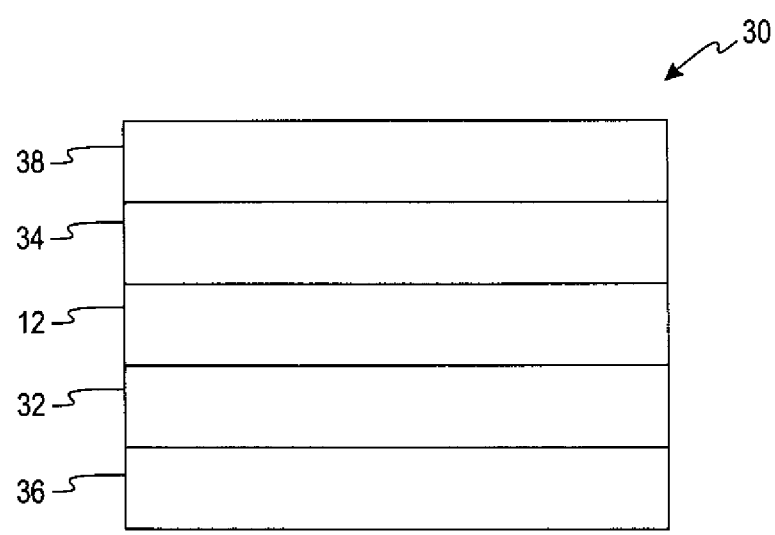
FIG. 3 is a five-layer pad according to one embodiment.

FIG. 3 illustrates a multi-layer pad 30 according to another embodiment. The multi-layer pad 30 includes the first layer 12, a second layer 32, a third layer 34, a fourth layer 36, and a fifth layer 38. The second layer 32 is adjacent to the first surface of the first layer 12 while the third layer 34 is adjacent to the second surface of the first layer 12. The fourth layer 36 is adjacent to the second layer 32 on the surface opposite the first layer 12. And the fifth layer 38 is adjacent to the third layer 34 on the surface opposite the first layer 12. The outer layers (the second layer 32, the third layer 34, the fourth layer 36 and the fifth layer 38) may be optimized for different purposes in much the same ways as the outer layers of the multi-layer pad 20 (the second layer 22 and the third layer 24) of FIG. 2 may be optimized for different purposes. The layers 34 and 38, 32 and 36, may be made from different or same materials. For example, the third layer 34 and the fifth layer 38 may be hydrogel layers. These layers 34, 38 may be developed from the same hydrophilic polymers while presenting different porosity to improve diffusion selectivity. In another example, one or both of the fourth layer 36 or fifth layer 38 may be another porous membrane, paper, and/or fabric material to improve the mechanical properties of the multi-layer pad 30.

As previously mentioned, the multi-layer pads 10, 20, or 30 are adapted to serve as an interface generally between and coupling the skin and the sensor according to one method. In one method, the sensor determines the concentration of the desired analyte from a sampling of the ISF. In one embodiment, the sensor is an electrochemical sensor.

Figure 4:
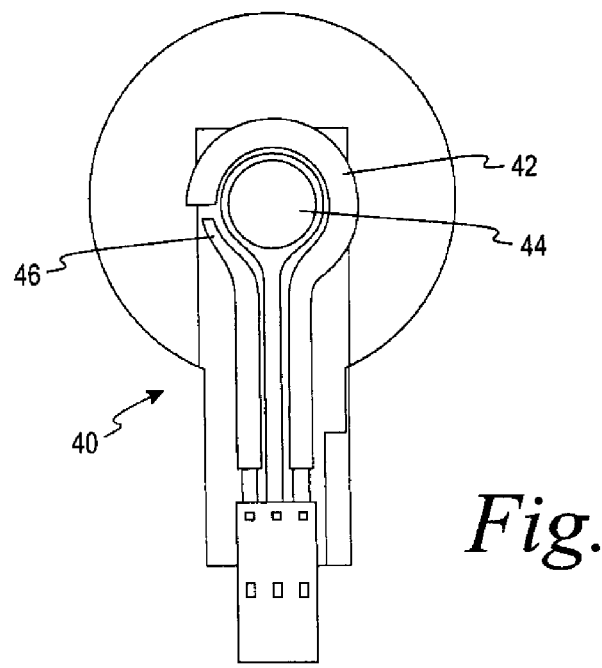
FIG. 4 is an electrochemical sensor according to one embodiment.

Referring to FIG. 4, an electrochemical sensor 40 is shown according to one embodiment. The electrochemical sensor 40 includes at least a counter electrode 42 and a working electrode 44. Other electrodes such as a detection electrode 46 may be included in the electrochemical sensor 40. It is contemplated that more or less electrodes can be formed in the method of the present invention. For example, the test sensor may include exactly two electrodes or at least three electrodes. The exactly two electrodes may be a working electrode and a counter electrode in which an electrochemically created current flow when these electrodes are electrically connected and a potential is created between them.

Figure 5:
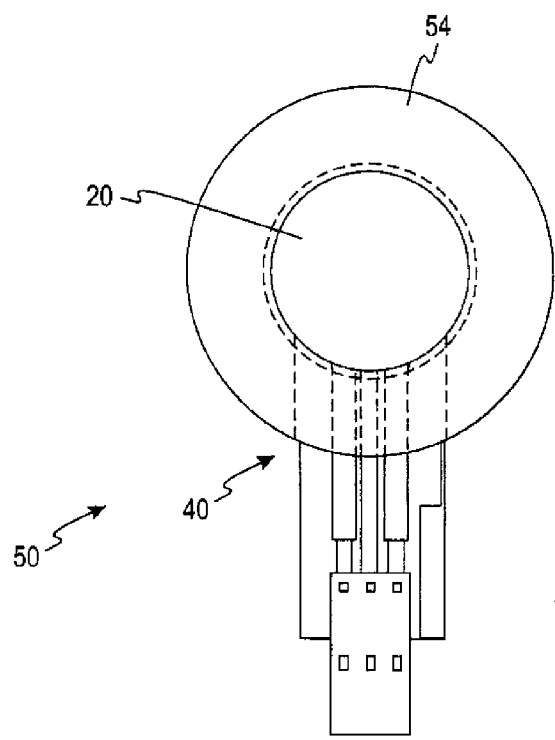
FIG. 5 is an electrochemical sensor system including the electrochemical sensor of FIG. 4 and the pad of FIG. 2.

As shown in FIG. 5, the electrochemical sensor system 50 includes the electrochemical sensor 40 of FIG. 4, the multi-layer pad 20 and an adhesive ring 54. In this embodiment, the adhesive ring 54 has two functions: (a) to cover a portion of the multi-layer pad 20 and secure it to the electrochemical sensor 40; and (b) to secure the electrochemical sensor system 50, including the multi-layer pad 20, to the skin.

In one method of determining an analyte concentration, a multi-layer pad (e.g., multi-layer pad 10, 20, or 30) is added to the skin. The multi-layer pad may be located at a skin site such as the volar forearm between the wrist and elbow. It is contemplated that the multi-layer pad may be located at other skin sites such as the abdomen. The skin may then be pretreated in this method to increase the skin permeability. One example of pre-treating is to use ultrasound energy to disrupt the lipid bilayer of the stratum corneum so as to increase the skin permeability. By increasing the skin permeability, the amount of diffused analyte from the dermis ISF is increased. This results in improved sampling of the analytes of interest (e.g., glucose) found in the ISF. A sensor determines the concentration of the desired analyte after contacting the multi-layer pad and the skin.

One non-limiting source of an ultrasound energy system is Sontra SonoPrep® ultrasonic skin permeation system marketed by Sontra Medical Corporation. The SonoPrep® system applies relatively low frequency ultrasonic energy to the skin for a limited duration (from about 10 to 20 seconds). The ultrasonic horn contained in the device vibrates at about 55,000 times per second (55 KHz) and applies energy to the skin through the liquid-coupling medium to create cavitation bubbles that expand and contract in the coupling medium. That cavitation results in the creation of cavities in the stratum cornium.

EXAMPLES

Example 1

5 g of glucose oxidase (GO) was dissolved in a phosphate-buffered saline solution containing 0.4 M of lactic acid at pH 7.2. Kimwiper® EX-L paper wiper from Kimberly-Clark was immersed in the 5 wt % GO solution for about 30 minutes at room temperature. The paper wiper was then removed from the GO solution and dried in a low humidity room at room temperature. The GO-containing paper wiper was then immersed in a monomer solution. The monomer solution contained 60 parts of N-vinyl pyrrolidone, 40 parts of vinyl acetate, 1 part of diethylene glycol divinyl ether, and 1 part of (2-hydroxy-4'-(2-hydroxyethoxy)-2-methylpropiopheone, which is an UV initiator. The co-polymerization was then initiated under UV irradiation. Upon completing the polymerization with no monomer left over, a three layer structure was formed. After hydrating the polymeric outer layers, the multi-layer pad is adapted to be directly used.

Example 2

5 g of glucose oxidase (GO) and 2 g of calcium chloride ($CaCl_2$) were dissolved in 93 g of nanopure water. Kimwiper® EX-L paper wiper from Kimberly-Clark was immersed in the GO—$CaCl_2$ solution for 30 minutes at room temperature. The paper wiper was then removed from the GO—$CaCl_2$ solution and dried in a low humidity room at room temperature. A solution containing 4 wt % of sodium alginate and 1 wt % of poly(ethylene oxide) was coated onto both sides of the GO—$CaCl_2$ treated paper wiper and then wrapped with a plastic wrap film. The coated film was then exposed to a temperature that ranged from about 2 to about 8° C. for a duration of up to 6 months. It is believed that calcium ions from the paper wiper eventually dissolved and diffused into the polymer solutions coated on both sides and crosslinked the sodium alginate. Alginate is a natural copolymer of two uronic acids, D-mannuronic acid and L-guluronic acid. While not being bound by theory, it is believed that calcium ions bind to the polymer whenever there are two neighboring guluronic acid residues and form an insoluble network.

Example 3

5 g of glucose oxidase (GO) and 95 g of phosphate-buffered saline solution. Kimwiper® EX-L paper wiper from Kimberly-Clark was immersed in the GO solution for about 30 minutes at room temperature. The paper wiper was then removed from the GO solution and dried in a low humidity room at room temperature. A solution containing 4 wt % of sodium alginate and 1 wt % of poly(ethylene oxide) was coated onto both sides of the GO-treated paper wiper. A 5 wt % of calcium chloride solution was then sprayed over each surface and the coated wiper was wrapped with plastic wrap film. The coated film was then exposed to a temperature that ranged from about 2 to about 8° C. for a duration of up to 6 months. While not being bound by theory, it is believed that calcium ions from the paper wiper eventually dissolved and diffused into the polymer solutions coated on both sides and crosslinked the sodium alginate so as to form an insoluble network.

Example 4

5 g of glucose oxidase (GO) was dissolved in 95 g of phosphate-buffered saline solution. Kimwiper® EX-L paper wiper from Kimberly-Clark was immersed in the GO solution for 30 minutes at room temperature. The paper wiper was then removed from the GO solution and dried in a low humidity room at room temperature. A solution containing 4 wt % of sodium alginate and 1 wt % of poly(ethylene oxide) was mixed with $CaCO_3$ powder. This mixture was then coated onto both sides of GO-treated paper wiper. An acetic acid solution was then sprayed over each surface and the coated wiper was wrapped with plastic wrap film. The coated film was then exposed to a temperature that ranged from about 2 to about 8° C. for a duration up to 6 months. While not being bound by theory, it is believed that calcium ions from the paper wiper eventually dissolved and diffused into the polymer solutions coated on both sides and cross-linked the sodium alginate so as to form an insoluble network.

Example 5

5 g of glucose oxidase (GO) was dissolved in 95 g of phosphate-buffered saline solution. Kimwiper® EX-L paper wiper from Kimberly-Clark was immersed in the GO solution for 30 minutes at room temperature. The paper wiper was then removed from the GO solution and dried in a low humidity room at room temperature. A 3 wt % of gelatin solution in nanopure water was coated onto both sides of the GO-treated paper wiper. Each surface of the paper wiper was then exposed under UV for 30 minutes at room temperature. Gelatin molecules were cross-linked with each other under UV irradiation so as to form an insoluble network.

Alternative Embodiment A

A multi-layer pad adapted to be used in determining an analyte concentration, the pad comprising:
a first layer including an enzyme, the enzyme being adapted to assist in determining the analyte concentration; and
a second layer being attached to the first layer, the second layer being made of a skin-conforming material.

Alternative Embodiment B

The pad of Alternative Embodiment A wherein the skin-conforming material comprises a hydrogel.

Alternative Embodiment C

The pad of Alternative Embodiment A wherein the skin-conforming material is a cross-linked hydrophillic polymer.

Alternative Embodiment D

The pad of Alternative Embodiment A wherein the second layer includes permeation enhancers, humectants, surfactants, or combinations thereof.

Alternative Embodiment E

The pad of Alternative Embodiment A wherein the first layer further includes fabric, porous membrane, or paper material.

Alternative Embodiment F

The pad of Alternative Embodiment E wherein the enzyme is physically absorbed on or in the fabric, porous membrane, or paper material.

Alternative Embodiment G

The pad of Alternative Embodiment E wherein the enzyme is chemically immobilized in the fabric, porous membrane, or paper material.

Alternative Embodiment H

The pad of Alternative Embodiment A wherein the enzyme is glucose oxidase.

Alternative Embodiment I

The pad of Alternative Embodiment A wherein the enzyme is glucose dehydrogenase.

Alternative Embodiment J

A multi-layer pad adapted to be used in determining an analyte concentration, the pad comprising:
a first layer including an enzyme, the enzyme being adapted to assist in determining the analyte concentration;
a second layer being made of a skin-conforming material; and
a third layer in which the first layer is located between the second layer and third layer.

Alternative Embodiment K

The pad of Alternative Embodiment J wherein the skin-conforming material comprises a hydrogel.

Alternative Embodiment L

The pad of Alternative Embodiment J wherein the skin-conforming material is a cross-linked hydrophillic polymer.

Alternative Embodiment M

The pad of Alternative Embodiment J wherein the second layer includes permeation enhancers, humectants, surfactants or combinations thereof.

Alternative Embodiment N

The pad of Alternative Embodiment J wherein the first layer further includes fabric, porous membrane, or paper material.

Alternative Embodiment O

The pad of Alternative Embodiment N wherein the enzyme is physically absorbed on or in the fabric, porous membrane, or paper material.

Alternative Embodiment P

The pad of Alternative Embodiment N wherein the enzyme is chemically immobilized in the fabric, porous membrane, or paper material.

Alternative Embodiment Q

The pad of Alternative Embodiment J wherein the enzyme is glucose oxidase.

Alternative Embodiment R

The pad of Alternative Embodiment J wherein the enzyme is glucose dehydrogenase.

Alternative Process S

A method of continuously determining an analyte concentration, the method comprising the acts of:
providing a multi-layer pad comprising a first layer and a second layer, the second layer being attached to the first layer, the first layer including an enzyme, the enzyme being adapted to assist in determining the analyte concentration, the second layer being made of a skin-conforming material;
providing a sensor that is adapted to assist in determining the analyte concentration;
placing the multi-layer pad on the skin, the multi-layer pad being located between the sensor and the skin; and
determining the analyte concentration.

Alternative Process T

The method of Alternative Process S wherein the skin is the volar forearm.

Alternate Process U

The method of Alternative Process S wherein the analyte is glucose.

Alternate Process V

The method of Alternative Process S wherein the sensor is an electrochemical sensor.

Alternative Process W

The method of Alternative Process S wherein the skin-conforming material comprises a hydrogel.

Alternative Process X

The method of Alternative Process S wherein the skin-conforming material is a cross-linked hydrophillic polymer.

Alternative Process Y

The method of Alternative Process S wherein the second layer includes permeation enhancers, humectants, surfactants, or combinations thereof.

Alternative Process Z

The method of Alternative Process S wherein the first layer further includes fabric, porous membrane, or paper material.

Alternative Process AA

The method of Alternative Process S wherein the enzyme is glucose oxidase.

Alternative Process AB

The method of Alternative Process S wherein the enzyme is glucose dehydrogenase.

Alternative Process AC

A method of continuously determining an analyte concentration, the method comprising the acts of:
providing a multi-layer pad comprising a first layer, a second layer, and a third layer, the second layer being made of a skin-conforming material, the first layer including an enzyme, the enzyme being adapted to assist in determining the analyte concentration, the first layer being located between the second layer and the third layer;
providing a sensor that is adapted to assist in determining the analyte concentration;
placing the multi-layer pad on the skin, the multi-layer pad being located between the sensor and the skin; and
determining the analyte concentration.

Alternative Process AD

The method of Alternative Process AC wherein the skin-conforming material comprises a hydrogel.

Alternative Process AE

The method of Alternative Process AC wherein the skin-conforming material is a cross-linked hydrophillic polymer.

Alternative Process AF

The method of Alternative Process AC wherein the second layer includes permeation enhancers, humectants, surfactants, or combinations thereof.

Alternative Process AG

The method of Alternative Process AC wherein the first layer further includes fabric, porous membrane, or paper material.

Alternative Process AH

The method of Alternative Process AC wherein the enzyme is glucose oxidase.

Alternative Process AI

The method of Alternative Process AC wherein the enzyme is glucose dehydrogenase.

Alternative Embodiment AJ

An electrochemical sensor system comprising:
an electrochemical sensor having a least a counter electrode and a working electrode;
a multi-layer pad coupled to the electrochemical sensor, the multi-layer pad comprising a first layer and a second layer, the second layer being attached to the first layer, the second layer being biocompatible for skin contact, the first layer including an enzyme, the enzyme being adapted to assist in determining the analyte concentration.

Alternative Embodiment AK

The sensor system of Alternative Embodiment AJ wherein the multi-layer pad is attached to the electrochemical sensor.

Alternative Embodiment AL

The sensor system of Alternative Embodiment AJ wherein the multi-layer pad is attached to the electrochemical sensor via an adhesive.

Alternative Embodiment AM

The sensor system of Alternative Embodiment AJ wherein the sensor further includes a third electrode.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A multi-layer pad adapted to be used in determining an analyte concentration, the pad comprising:
    a first layer including an enzyme, the first layer comprising material selected from the group consisting of fabric, porous membrane, and paper material, the enzyme being adapted to assist in determining the analyte concentration; and
    a second layer being chemically cross-linked to the first layer, the second layer being made of a skin-conforming material.

2. The pad of claim 1, wherein the skin-conforming material comprises a hydrogel.

3. The pad of claim 1, wherein the skin-conforming material is a cross-linked hydrophilic polymer.

4. The pad of claim 1, wherein the enzyme is physically absorbed on or in the selected material.

5. The pad of claim 1, wherein the enzyme is chemically immobilized in the selected material.

6. The pad of claim 1, wherein the enzyme is glucose oxidase or glucose dehydrogenase.

7. The pad of claim 1, further comprising a third layer in which the first layer is located between the second layer and third layer, the second and the third layers being chemically cross-linked to the first layer.

8. The pad of claim 1, wherein the first layer comprises a layer of porous membrane including cellulose, cellulose derivatives, nylon, polyacrylonitrile, polycarbonate, polypropylene, polysulfone, or polyvinyl chloride.

9. The pad of claim 1, wherein the first layer comprises a layer of paper material.

10. The pad of claim 9, wherein the paper material includes cellulose or cellulose derivatives.

11. The pad of claim 1, wherein the first layer comprises a layer of fabric and the enzyme is added to the fabric.

12. The pad of claim 11, wherein the fabric includes silk, cellulose, polyethylene terephtalate, polyurethane, or glass fibers.

13. A method of continuously determining an analyte concentration, the method comprising the acts of:

providing a multi-layer pad comprising a first layer and a second layer, the second layer being chemically cross-linked to the first layer, the first layer including an enzyme, the first layer comprising material selected from the group consisting of fabric, porous membrane, and paper material, the enzyme being adapted to assist in determining the analyte concentration, the second layer being made of a skin-conforming material;

providing a sensor that is adapted to assist in determining the analyte concentration;

placing the multi-layer pad on skin, the multi-layer pad being located between the sensor and the skin; and determining the analyte concentration.

14. The method of claim 13, wherein the sensor is an electrochemical sensor.

15. The method of claim 13, wherein the multi-layer pad further comprises the first layer being located between the second layer and the third layer, the third layer being chemically cross-linked to the first layer.

16. The method of claim 13, wherein the first layer comprises a layer of porous membrane including cellulose, cellulose derivatives, nylon, polyacrylonitrile, polycarbonate, polypropylene, polysulfone, or polyvinyl chloride.

17. The method of claim 13, wherein the first layer comprises a layer of paper material including cellulose or cellulose derivatives or the first layer is a layer of fabric including silk, cellulose, polyethylene terephtalate, polyurethane, or glass fibers.

18. An electrochemical sensor system comprising:

an electrochemical sensor having at least a counter electrode and a working electrode; and a multi-layer pad coupled to the electrochemical sensor, the multi-layer pad comprising a first layer and a second layer, the second layer being chemically cross-linked to the first layer, the second layer being biocompatible for skin contact, the first layer including an enzyme, the first layer comprising material selected from the group consisting of fabric, porous membrane, and paper material, the enzyme being adapted to assist in determining the analyte concentration, wherein the multi-layer pad is attached to the electrochemical sensor.

19. The system of claim 18, wherein the first layer comprises a layer of porous membrane including cellulose, cellulose derivatives, nylon, polyacrylonitrile, polycarbonate, polypropylene, polysulfone, or polyvinyl chloride.

20. The system of claim 18, wherein the first layer comprises a layer of paper material including cellulose or cellulose derivatives or the first layer is a layer of fabric including silk, cellulose, polyethylene terephtalate, polyurethane, or glass fibers.

* * * * *